United States Patent
Lee et al.

(10) Patent No.: US 10,537,559 B2
(45) Date of Patent: Jan. 21, 2020

(54) ISONITRAMINE COMPOUND AND COMPOSITION CONTAINING SAME FOR PREVENTING OR TREATING METABOLIC DISEASES

(71) Applicant: INJE UNIVERSITY INDUSTRY-ACADEMIC COOPERATION FOUNDATION, Gimhae-si, Gyeongsangnam-do (KR)

(72) Inventors: Hyo-Jong Lee, Gimhae-si (KR); Yohan Park, Gimhae-si (KR); Hyeung-Geun Park, Seoul (KR)

(73) Assignee: INJE UNIVERSITY INDUSTRY ACADEMIC COOPERATION FOUNDATION, Gimhae-si, Gyeongsangnam-do (KR)

( * ) Notice: Subject to any disclaimer, the term of this patent is extended or adjusted under 35 U.S.C. 154(b) by 0 days.

(21) Appl. No.: 16/161,094

(22) Filed: Oct. 16, 2018

(65) Prior Publication Data

US 2019/0209534 A1   Jul. 11, 2019

Related U.S. Application Data

(63) Continuation of application No. 15/752,592, filed as application No. PCT/KR2016/009036 on Aug. 17, 2016, now abandoned.

(30) Foreign Application Priority Data

Aug. 17, 2015  (KR) ........................ 10-2015-0115504
Aug. 17, 2016  (KR) ........................ 10-2016-0104145

(51) Int. Cl.

| | | |
|---|---|---|
| A61K 31/438 | (2006.01) | |
| A23L 29/00 | (2016.01) | |
| A61P 3/04 | (2006.01) | |
| A61P 3/06 | (2006.01) | |
| A61P 3/10 | (2006.01) | |
| C07D 221/20 | (2006.01) | |

(52) U.S. Cl.
CPC .......... *A61K 31/438* (2013.01); *A23L 29/045* (2016.08); *A61P 3/04* (2018.01); *A61P 3/06* (2018.01); *A61P 3/10* (2018.01); *C07D 221/20* (2013.01); *A23V 2002/00* (2013.01); *A23V 2200/328* (2013.01); *A23V 2200/332* (2013.01)

(58) Field of Classification Search
None
See application file for complete search history.

(56) References Cited

U.S. PATENT DOCUMENTS

2007/0213314 A1   9/2007   Chang et al.

FOREIGN PATENT DOCUMENTS

| KR | 10-1059274 B1 | 8/2011 |
| KR | 10-1509055 B1 | 4/2015 |

OTHER PUBLICATIONS

Pandey et al. Eur. J. Org. Chem. (2011), 7372-7377.*
Schafer et al. Drug Discovery Today, 2008, 13 (21/22), 913-916.*
Hong et al. Journal of Translational Medicine 2004, 2(44), p. 1-8.*
International Search Report for PCT/KR2016/009036 dated Dec. 13, 2016 from Korean Intellectual Property Office.
Park et al., "Highly Enantioselective Total Synthesis of (+)-Isonitramine", Organic Letters, 2012 [E-pub.: Jan. 17, 2012], vol. 14, No. 2, pp. 852-854.
Hellberg, L. H. et al., "Synthesis of the spirocyclic alkaloid nitramine", Tetrahedron Letters, 1986, vol. 27, No. 34, pp. 3955-3956.
Kozikowski A.P. et al., "The Intramolecular Nitrile Oxide Cycloaddition Route to Spirocyclic Alkaloids. A Total Synthesis of Isonitramine and Sibirine", Journal of the Chemical Society, Chemical Communications, 1985, vol. 13, pp. 847-848.
Osmanov, Z. et al., "Structure of sibirine", Chemistry of Natural Compounds, 1982, vol. 18, No. 2, pp. 206-208.
Vincent J. Carey et al., "Body Fat Distribution and Risk of Non-Insulin-dependent Diabetes Mellitus in Women", American Journal of Epidemiology, 1997, vol. 145, No. 7, pp. 614-619.
Pandey et al. Eur. J. of Org. Chem., (2011), p. 7372-7377.
Alonso et al. Synlett (2005) v.11, p. 1726-1730.
Hotamisligil GS. et al., "Tumor Necrosis Factor α: A Key Component of the Obesity-Diabetes Link", Diabetes, 43, pp. 1271-1278, Nov. 1994.

* cited by examiner

*Primary Examiner* — Yong L Chu
(74) *Attorney, Agent, or Firm* — Revolution IP, PLLC

(57) ABSTRACT

Provided are a pharmaceutical composition for preventing or treating metabolic diseases and a health food for alleviating metabolic diseases, each of which the pharmaceutical composition and the health food includes, a stereoisomer of isonitramine or a derivative thereof, or a racemic mixture of the stereoisomers, wherein such a compound exhibits effects of inhibiting fat content or differentiation of an adipocyte, inhibiting activity of a carbohydrate metabolism enzyme, protecting pancreas, inhibiting blood sugar, and promoting insulin secretion, and thus can be favorably utilized in the treatment of metabolic diseases, such as obesity, diabetes, and hyperlipidemia.

2 Claims, 8 Drawing Sheets

Specification includes a Sequence Listing.

(+)-isonitramine (1)

compound 2 compound 3 compound 4 compound 5 compound 6

```
                           SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gtgatggaag accactcgca t                                             21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
accattgggt cagctcttgt g                                             21

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
aggtgctgga gttgaccagt g                                             21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ccggaatctc ctagtcctgg c                                             21

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
aaggtgaaga gcatcataac cct                                           23

<210> SEQ ID NO 6
<211> LENGTH: 23
<212> TYPE: DNA
<213> ORGANISM: Artificial Sequence
<220> FEATURE:
<223> OTHER INFORMATION: Primer
```

<400> SEQUENCE: 6
tcacgccttt cataacacat tcc                                    23

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gggagtttgg ctccagagtt t                                      21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tgtgtcttca ggggtcctta g                                      21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
tgttcctctt aatcctgccc a                                      21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ccaacctgca caagttccct t                                      21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
agagggaaat cgtgcgtgac                                        20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ggccgtcagg cagctcatag                                        20

<210> SEQ ID NO 13
<211> LENGTH: 32

```
<212> TYPE: DNA
<213> ORGANISM: Artificial Sequence
<220> FEATURE:
<223> OTHER INFORMATION: Primer

<400> SEQUENCE: 13
gagaattctc acacacacac acgtgagcag ta                              32

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
gtaaaagctt tccgccataa catctccagc agaa                            34

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
agtgtaagca ctaacccagg caca                                       24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
tgcaaagtca gccacctcag tttc                                       24

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
cgagcaggag atgggaacc                                             19

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
caacggaaac gctcattgc                                             19
```

ISONITRAMINE COMPOUND AND COMPOSITION CONTAINING SAME FOR PREVENTING OR TREATING METABOLIC DISEASES

CROSS REFERENCE TO PRIOR APPLICATION

This application is a Continuation Application of U.S. patent application Ser. No. 15/752,592 filed on Apr. 26, 2018 under 35 U.S.C. § 120, which is the 35 U.S.C. § 371 national stage of International application PCT/KR2016/009036 filed on Aug. 17, 2016, which claims priority to Korean applications 10-2015-0115504 filed on Aug. 17, 2015 and 10-2016-0104145 filed on Aug. 17, 2016, respectively.

BACKGROUND

The present invention relates to a composition for preventing or treating a metabolic disease, the composition including a stereoisomer of isonitramine or a derivative thereof, or a racemic mixture of the stereoisomers.

As the standard of living improves with the development of the economy, the number of modern people who belong to obesity, which is the main cause of metabolic diseases, is rapidly increasing. In particular, it is recently reported that one third of Americans and 20% of children are obese patients in the United States. That is, these statistics do not simply mean the increase in the numbers, but also mean that health threats of modern people have increased.

In this regard, the facts that obesity is associated with a high incidence of metabolic disorders of carbohydrates and diseases such as non-insulin dependent diabetes mellitus (NIDDM, type II diabetes), and that weight gain exacerbates existing diabetes have been reported. In addition, a number of studies have shown that obesity precedes impaired glucose tolerance (IGT) and diabetes (see Carey V J. et al., Body fat distribution and risk of non-insulin-dependent diabetes mellitus in women, The nurses' health study, Am J Epidemiol, 145, pp. 614-619, 1997). For example, Framingham's study found the frequent occurrence of IGT in obese people while most other studies found that obese people with IGT are high-risk people for the occurrence of NIDDM.

According to a glucose tolerance test (GTT) that is one of methods of diagnosing diabetes and measures blood glucose before and after eating a certain amount of glucose, many obese patients show normal blood glucose response, but also show increased insulin resistance which causes insulin secretion response more frequently than normal people. Such insulin resistance is one of main symptoms of obesity and NIDDM, and is observed from the beginning of obesity.

Although various hypotheses about the mechanism of decreased insulin metabolism in obesity have been proposed, but there is no definite mechanism yet. However, an insulin receptor related to the insulin metabolism, a glucose transporter, an enzymes related to glycogenesis and glycolysis have been observed to decrease in the insulin metabolism, and in this regard, the decrease in the insulin metabolism is understood as a secondary phenomenon caused by obesity (Golay A. et al., Obesity and NIDDMP, the retrograde regulation concept, Diabetes Rev, 5, pp. 69-82, 1997).

Meanwhile, the recently published reports show that metabolic messengers or factors secreted from adipocytes increase insulin resistance by inhibiting the insulin metabolism in muscles and liver. Here, the most representative factor is free fatty acid (FFA), which is produced by hydrolysis of fatty acids in triglycerides stored in an adipose tissue. In addition, TNF and leptin that are secreted from adipocytes are suggested to cause insulin resistance (Hotamisligil G S. et al., Tumor necrosis factor a, a key component of the obesity-diabetes link, Diabetes, 43, pp. 1271-12'78, 1994).

In obesity, lipid is the main energy metabolism with lipid degradation and lipid synthesis that are both increased. The increase in lipid degradation and consequent increased use of FFAs are the most significant features of obesity, especially abdominal obesity. High correlation between lipid volume and lipid oxidation is observed, suggesting that the increase in lipid volume is considered as a cause of increased serum FFA and lipid oxidation.

Furthermore, more than 70% of people with type II diabetes are obese, and the risk of developing other diseases such as hypertension, hyperlipidemia, and some cancers are reported to be increased from obesity.

However, to date, there has not been developed a drug for the treatment of metabolic diseases, and attempts to treat metabolic diseases using drugs for treating diabetes, hyperlipidemia, and hypertension have limitations as medicines.

Therefore, it is necessary to develop technologies that can effectively prevent and treat metabolic diseases by more efficiently controlling the induction mechanism of obesity and metabolic diseases induced by obesity.

In this regard, the present inventors have completed the present disclosure by confirming that a pharmaceutical composition and a health food have excellent effects of treating metabolic diseases, each of which includes, as an active ingredient, a stereoisomer of isonitramine or a derivative thereof, or a racemic mixture of the stereoisomers.

Therefore, the present disclosure is aimed to provide a pharmaceutical composition and a health food for preventing or treating a metabolic disease, each of which includes, as an active ingredient, a stereoisomer of isonitramine or a derivative thereof, or a racemic mixture of the stereoisomers.

SUMMARY

The achieve the objects of the present disclosure, the present disclosure provides a pharmaceutical composition or a health food for preventing or treating a metabolic disease, each of which includes, as an active ingredient, a stereoisomer represented by Formula 1 or a racemic mixture thereof:

[Formula 1]

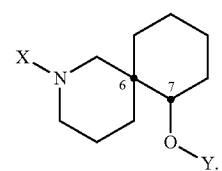

In Formula 1,

X may be selected from the group consisting of hydrogen, a $C_1$-$C_{10}$ alkyl group, an acyl group, an allyl group, and a benzyl group, wherein, when X is an allyl group, one or more halogen may be substituted for the unsaturated carbon, or when X is

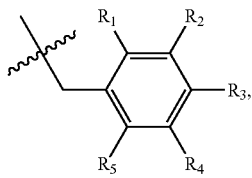

$R_1$ to $R_5$ may each independently be a hydrogen atom, a nitro group, a halogen atom, a cyano group, a hydroxyl group, a dimethylamino group, a methylsulfonylamide group, a trifluoromethyl group, a C1-C3 alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

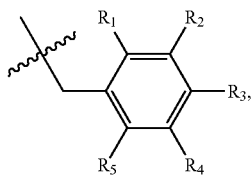

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and carbon atoms at the $6^{th}$ position and the $7^{th}$ position may each be a chiral center.

In addition, the present disclosure provides a pharmaceutical composition or a health food for preventing or treating a metabolic disease, each of which includes, as an active ingredient, a stereoisomer represented by Formula 2 or a racemic mixture thereof.

[Formula 2]

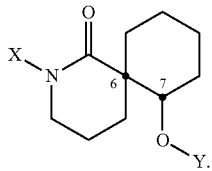

In Formula 2,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

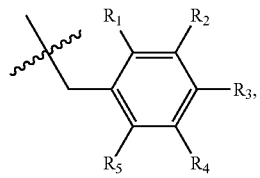

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

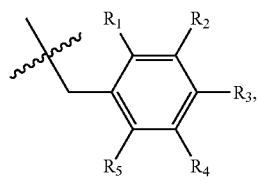

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and carbon atoms at the $6^{th}$ position and the $7^{th}$ position may each be a chiral center.

In addition, the present disclosure provides a pharmaceutical composition or a health food for preventing or treating a metabolic disease, each of which includes, as an active ingredient, a stereoisomer represented by Formula 3 or a racemic mixture thereof.

[Formula 3]

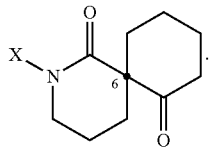

In Formula 3,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

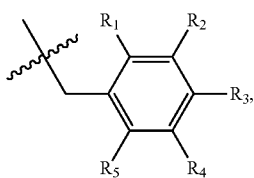

R₁ to R₅ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

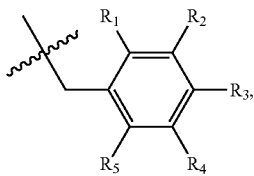

R₁ to R₅ may may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and a carbon atom at the 6$^{th}$ position may be a chiral center.

According to the present disclosure, a stereoisomer of isonitramine or a derivative thereof, or a racemic mixture of the stereoisomers exhibits effects of inhibiting a fat content or differentiation of an adipocyte, inhibiting activity of a carbohydrate metabolism enzyme, protecting pancreas, inhibiting blood sugar, and promoting insulin secretion, and thus, can be favorably used as a pharmaceutical composition or a health food for preventing or treating a metabolic disease.

DETAILED DESCRIPTION

Figure 1:
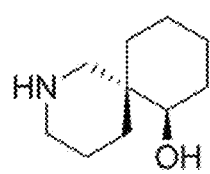
FIG. 1 shows structural formulae of (+)-isonitramine stereoisomer ((+)-isonitramine (1)) according to an embodiment and Compounds 2 to 6 thereof.
Figure 1:
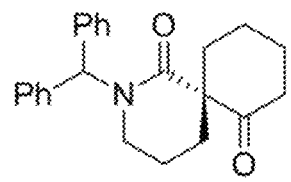
Figure 1:
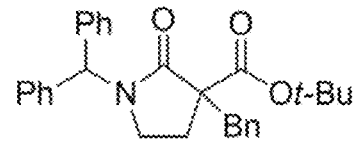
Figure 1:
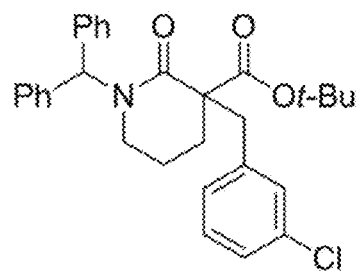
Figure 1:
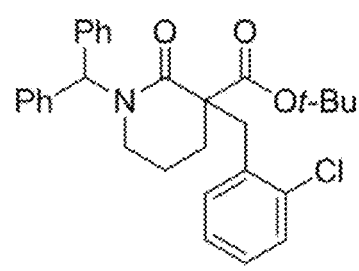
Figure 1:
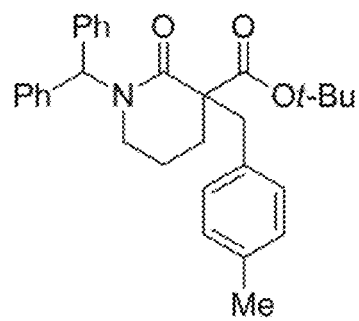

While synthesizing a stereoisomer of isonitramine or a derivative thereof and studying the synthesis, the inventors of the present disclosure completed the present disclosure by confirming that such synthetic products exhibit effects of inhibiting a fat content or differentiation of an adipocyte, inhibiting activity of a carbohydrate metabolism enzyme, protecting pancreas, inhibiting blood sugar, and promoting insulin secretion.

Therefore, the present disclosure provides a pharmaceutical composition for preventing or treating a metabolic disease, the pharmaceutical composition including, as an active ingredient, a stereoisomer represented by Formula 1 or a racemic mixture thereof:

[Formula 1]

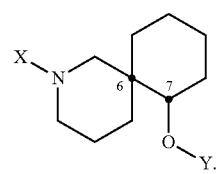

In Formula 1,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

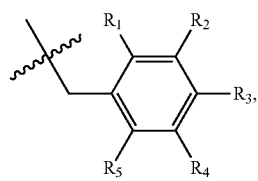

R₁ to R₅ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

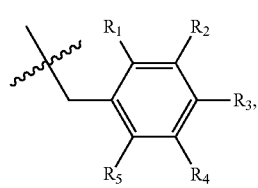

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and carbon atoms at the $6^{th}$ position and the $7^{th}$ position may each be a chiral center.

Here, the term 'stereoisomer' as used herein refers to a molecule that has the same molecular formula and sequence of constituent atoms, but differs in arrangement of these atoms in space. That is, the stereoisomer produced by chiral centers at the $6^{th}$ position and the $7^{th}$ position of Formula 1 may be a (6R, 7R), (6R, 7S), (6S, 7S), or (6S, 7R) type.

The term 'racemic mixture' as used herein refers a mixture of (+)- and (−)-isomers at an equal amount, i.e., 50:50. Therefore, the racemic mixture may be a mixture of stereoisomers (6R, 7R) and (6S, 7S) of Formula 1 at a ratio of 50:50 or a mixture of stereoisomers (6R, 7S) and (6S, 7R) of Formula 1 at a ratio of 50:50.

In addition, the present disclosure provides a health food for preventing or alleviating a metabolic disease, the health food including, as an active ingredient, a stereoisomer represented by Formula 1 or a racemic mixture thereof:

[Formula 1]

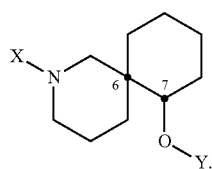

In Formula 1,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

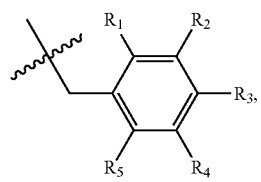

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

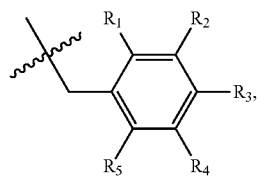

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and carbon atoms at the $6^{th}$ position and the $7^{th}$ position may each be a chiral center.

That is, the stereoisomer produced by chiral centers at the $6^{th}$ position and the $7^{th}$ position of Formula 1 may be a (6R, 7R), (6R, 7S), (6S, 7S), or (6S, 7R) type.

In addition, the racemic mixture may be a mixture in which the stereoisomers (6R, 7R) and (6S, 7S) of Formula 1 are mixed at a ratio of 50:50 or a mixture in which the stereoisomers (6R, 7S) and (6S, 7R) of Formula 1 are mixed at a ratio of 50:50.

Furthermore, the present disclosure provides a pharmaceutical composition for preventing and treating a metabolic disease, the pharmaceutical composition including, as an active ingredient, a stereoisomer represented by Formula 2 or a racemic mixture thereof:

[Formula 2]

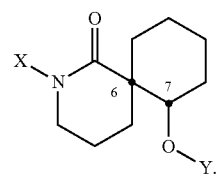

In Formula 2,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

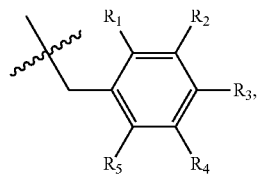

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

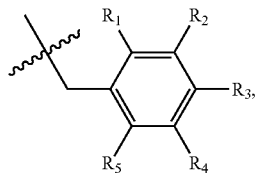

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and carbon atoms at the 6$^{th}$ position and the 7$^{th}$ position may each be a chiral center.

That is, the stereoisomer produced by chiral centers at the 6$^{th}$ position and the 7$^{th}$ position of Formula 2 may be a (6R, 7R), (6R, 7S), (6S, 7S), or (6S, 7R) type.

In addition, the racemic mixture may be a mixture in which the stereoisomers (6R, 7R) and (6S, 7S) of Formula 2 are mixed at a ratio of 50:50 or a mixture in which the stereoisomers (6R, 7S) and (6S, 7R) of Formula 2 are mixed at a ratio of 50:50.

In addition, the present disclosure provides a health food for preventing or alleviating a metabolic disease, the health food including, as an active ingredient, a stereoisomer represented by Formula 2 or a racemic mixture thereof:

[Formula 2]

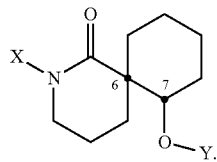

In Formula 2,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

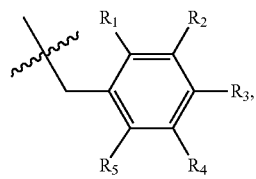

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

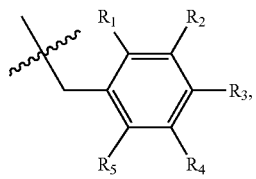

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and carbon atoms at the 6th position and the 7th position may each be a chiral center.

That is, the stereoisomer produced by chiral centers at the 6$^{th}$ position and the 7$^{th}$ position of Formula 2 may be a (6R, 7R), (6R, 7S), (6S, 7S), or (6S, 7R) type.

In addition, the racemic mixture may be a mixture in which the stereoisomers (6R, 7R) and (6S, 7S) of Formula 2 are mixed at a ratio of 50:50 or a mixture in which the stereoisomers (6R, 7S) and (6S, 7R) of Formula 2 are mixed at a ratio of 50:50.

Furthermore, the present disclosure provides a pharmaceutical composition for preventing and treating a metabolic disease, the pharmaceutical composition including, as an active ingredient, a stereoisomer represented by Formula 3 or a racemic mixture thereof:

[Formula 3]

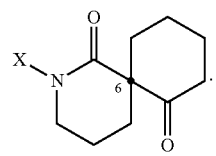

In Formula 3,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

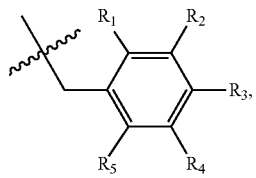

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

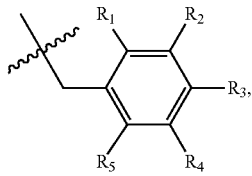

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and a carbon atom at the $6^{th}$ may be a chiral center.

That is, the stereoisomer produced by a chiral center at the $6^{th}$ position of Formula 3 may be a (R) or (S) type.

In addition, the racemic mixture may be a mixture in which the stereoisomers (R) and (S) of Formula 3 are mixed at a ratio of 50:50.

In addition, the present disclosure provides a health food for preventing or alleviating a metabolic disease, the health food including, as an active ingredient, a stereoisomer represented by Formula 3 or a racemic mixture thereof:

[Formula 3]

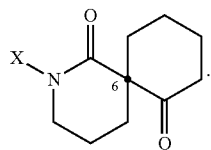

In Formula 3,

X may be selected from the group consisting of a hydrogen atom, a $C_1$-$C_{10}$ alkyl group, an acyl group, an allyl group, and a benzyl group, wherein, when X is an allyl group, one or more halogen may be substituted for the unsaturated carbon, or when X is

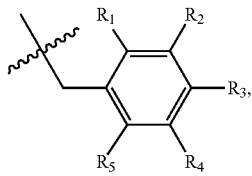

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group;

Y may be selected from the group consisting of a hydrogen atom, a $C_1$-$C_{10}$ alkyl group, an acyl group, an allyl group, and a benzyl group, wherein, when Y is an allyl group, one or more halogen may be substituted for the unsaturated carbon, or when Y is

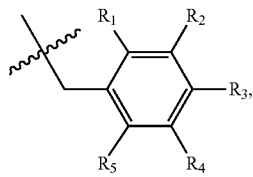

$R_1$ to $R_5$ may each independently be a hydrogen atom, a nitro group, a halogen atom, a cyano group, a hydroxyl group, a dimethylamino group, a methylsulfonylamide group, a trifluoromethyl group, a $C_1$-$C_3$ alkyl group, a $C_1$-$C_3$ alkoxy group, a vinyl group, an aryl group, a phenoxy group, or a benzoxy group; and a carbon atom at the $6^{th}$ position may be a chiral center.

That is, the stereoisomer produced by a chiral center at the $6^{th}$ position of Formula 3 may be a (R) or (S) type.

In addition, the racemic mixture may be a mixture in which the stereoisomers (R) and (S) of Formula 3 are mixed at a ratio of 50:50.

The metabolic disease may be selected from the group consisting of obesity, diabetes, hyperlipidemia, hypertriglyceridemia, liver disease, arteriosclerosis, stroke, myocardial infarction, cardiovascular disease, hyperglycemia, insulin resistance, and hyperinsulinemia, but is not limited thereto.

The pharmaceutical composition may be provided in one or more formulations selected from the group consisting of gels, emulsions, injections, powders, granules, aerosols, pasts, percutaneous absorbers, and patches according to a conventional method, but is not limited thereto.

In an embodiment, the pharmaceutical composition may further include at least one additive selected from the group consisting of suitable carriers, excipients, disintegrants, sweeteners, coatings, swelling agents, lubricants, flavoring agents, antioxidants, buffers, bacteriostats, diluents, dispersants, surfactants, binders, and lubricants that are typically used in the preparation of the pharmaceutical composition.

In detail, examples of the carriers, excipients, and diluents may include lactose, dextrose, sucrose, sorbitol, mannitol, xylitol, erythrytol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxylbenzoate, talc, magnesium stearate, mineral oil and the like. The solid formulations for oral administration may include tablet, pill, powder, granule, capsule and the like, and may be prepared by mixing the composition with at least one excipient, such as starch, calcium carbonate, sucrose, lactose, gelatin and the like. In addition, besides simple excipients, the lubricants, such as magnesium stearate, talc and the like may be used. The liquid formulations for oral administration may include suspension, solution, emulsion, syrup and the like. Besides simple diluents including water, liquid paraffin and the like, various excipients, such as wetting agent, sweetening agent, flavoring agent, preserving agent and the like may be used. The formulations for parenteral administration may include sterile aqueous solution, non-aqueous solvent, suspending agent, emulsifying agent, freeze-drying agent, suppository and the like. Examples of the suspending agent and non-aqueous solvent may include propylene glycol, polyethylene glycol, plant oil, such as olive oil, injectable ester, such as ethyl oleate, and the like. The base material for suppository may be witepsol, macrogol, tween 61, cacao oil, laurin oil, glycerol gelatin and the like.

A desirable dose of the stereoisomer or the racemic mixture thereof may vary depending on the condition and body weight of a subject, the type and severity of diseases, the drug form, and the administration route and period, and may be appropriately selected by one of ordinary skill in the art. According to an embodiment, although not limited thereto, a daily dose may be in a range of about 0.01 mg/kg to about 200 mg/kg, for example, about 0.1 mg/kg to about 200 mg/kg, and for example, about 0.1 mg/kg to about 100 mg/kg. The administration may be carried out once a day, or divided into several times. Here, the scope of the present disclosure is not limited thereto.

The term 'subject' as used herein may refer to a mammal including human, but is not limited thereto.

The health food may be provided in the form of powders, granules, tablets, capsule, syrup, or beverage. The health food may be used together with other foods and food additives in addition to the stereoisomer or the racemic mixture thereof, which is used as the active ingredient, and may be suitably used according to a conventional method. Here, the amount of the active ingredient may be appropriately determined according to the purpose of use, for example, prevention, health, or therapeutic treatment.

The effective dose of the stereoisomer or the racemic mixture thereof included in the health food may be used in accordance with the effective dose of the pharmaceutical composition. However, when used for the purpose of health and hygiene, or for long-term consumption for health control purposes, the effective dose of the active ingredient may be less than the above ranges. Since the active ingredient has no problem in terms of safety, it is clear that the active ingredient can be used in an amount within the ranges described above.

Types of the health food are not particularly limited, and examples thereof may include meat, sausage, bread, chocolate, candy, snack, cookie, pizza, ramen, other noodles, gum, dairy products including ice cream, various types of soups, beverages, teas, drinks, and alcoholic beverages, and a vitamin complex.

Hereinafter, to promote understanding of the present disclosure, reference has been made to Examples below. These Examples are provided so that the present disclosure will be thorough and complete, and will fully convey the concept of embodiments to one or ordinary skill in the art. In addition, these Examples are illustrated for convenience of explanation only, and thus, the scope of the present disclosure is not limited to Examples below.

<Example 1> Synthesis of Stereoisomer of Isonitramine or Derivatives of Isonitramine According to the methods disclosed in the documents in the related art by the present inventors, the present inventors synthesized a stereoisomer of isonitramine of a derivative of isonitramine.

A stereoisomer of (+)-isonitramine ((+)-isonitramine 1) or Compound 2 was synthesized according to the document already disclosed in the art Org. Lett. 2012, 14, 852-854).

In addition, Compound 3 to 6 were synthesized according to the document already disclosed in the art (Adv. Synth. Catal. 2011, 353, 3313-3318).

<Example 2> Inhibitory Effects of Isonitramine Derivatives on Fat Accumulation and Adipocyte Differentiation 1. Cell Culture and Differentiation 3T3-L1 mouse preadipocytes were cultured in a Dulbecco's modified Eagle's medium (DMEM) supplemented with 10% newborn calf serum (Gibco BRL, NY, USA) and antibiotics (100 U/ml penicillin and 100 µg/ml streptomycin, Gibco BRL, NY, USA) in an incubator under humidification conditions of a temperature of 37 r and 5% $CO_2$.

Afterwards, the cultured 3T3-L1 mouse cells were treated with 0.5 mM 1-methyl-3-isobutylxanthine purchased from Sigma (St. Louis, Mo.), 1 µM dexamethasone, 1 µg/mL insulin, and 10% fetal bovine serum (FBS, Gibco BRL), and then, cultured for 2 days to induce differentiation. After 2 days, the cultured medium was replaced with a fresh DMEM supplemented with 10% FBS and 1 µg/mL insulin. For the next 4 days, the cultured medium was replaced with a fresh DMEM supplemented with 10% FBS every day.

After 8 days, 90% or more of the cultured cells showed adipocyte phenotype.

2. Reverse Transcriptase-Polymerase Chain Reaction (RT-PCR)

According to the manufacturer's instructions, total cell RNA of the undifferentiated adipocytes and differentiated adipocytes was extracted by using Trizol (available from Invitrogen).

The RNA (4 µg) was reverse-transcribed into cDNA by using M-MLV reverse transcriptase (available from Promega). Accordingly, the expression of peroxisome proliferator-activated receptor γ (PPARγ), CCAAT/enhancer binding protein-α (C/EBPα), adipocyte protein 2 (aP2), lipoprotein lipase (LPL), and adiponectin was each confirmed.

Primers used herein are listed in Table 1 and were purchased from Bioneer.

TABLE 1

| Name | Direction | Sequence | SEQ ID NO: |
|---|---|---|---|
| PPARγ | Forward | GTGATGGAAGACCACTCGCAT | 1 |
|  | Reverse | ACCATTGGGTCAGCTCTTGTG | 2 |
| C/EBPα | Forward | AGGTGCTGGAGTTGACCAGTG | 3 |
|  | Reverse | CCGGAATCTCCTAGTCCTGGC | 4 |
| aP2 | Forward | AAGGTGAAGAGCATCATAACCCT | 5 |
|  | Reverse | TCACGCCTTTCATAACACATTCC | 6 |
| LPL | Forward | GGGAGTTTGGCTCCAGAGTTT | 7 |
|  | Reverse | TGTGTCTTCAGGGGTCCTTAG | 8 |
| Adiponectin | Forward | TGTTCCTCTTAATCCTGCCCA | 9 |
|  | Reverse | CCAACCTGCACAAGTTCCCTT | 10 |
| β-actin | Forward | AGAGGGAAATCGTGCGTGAC | 11 |
|  | Reverse | GGCCGTCAGGCAGCTCATAG | 12 |

The variable number of cycles was used to identify the amplification occurred in the linear phase.

In the PCR amplification, β-actin was used as an internal control group. The PCR products were separated by using 2.0% agarose gel, followed by being visualized by RedSafe nucleic acid staining (available from Intron, Korea) and UV irradiation.

3. Nile Red Staining

The undifferentiated or differentiated cells were washed three times with phosphate-buffered saline (PBS), and then, fixed with 4% 4-formaldehyde (PFA) at room temperature for 1 hour. Afterwards, the resulting cells were washed three times with PBS, and stained with 0.5 μg/ml of nile red (available from Sigma, St. Louis, Mo.) for 10 minutes. Following the completion of the staining, the resulting cells were washed with PBS, and the nuclei thereof were stained again with 4'-6-diamidino-2-phenylindole, (DAPI, available from Invitrogen). Images were obtained by using a phase contrast microscope (Axiovert M200 microscope, Zeiss).

4. Analysis of Triglyceride Concentration

The concentration of triglyceride in the cells was measured by using a triglyceride reagent purchased from Sigma and a free glycerol reagent.

The adipocytes were differentiated for 8 days with (+)-isonitramine 1 at a concentration of 100 μM or 500 μM, in a 6-well plate.

To analyze the concentration of triglyceride in the cells, the cells were washed with PBS, and then, lysed with 100 μl of a lysis buffer. 20 μl of the lysate was mixed with 20 μl of the triglyceride reagent, followed by being cultured for 30 minutes at a temperature of 37° C. Afterwards, 30 μl of the cultured mixture was loaded to a 96-well plate, and 100 μl of the free glycerol reagent was added to the plate, followed by being cultured for 5 minutes at a temperature of 37° C.

Following the completion of the culturing, the absorbance of the cells was measured by using a spectrophotometer at a wavelength of 540 nm.

5. Experiment Results

Figure 2:
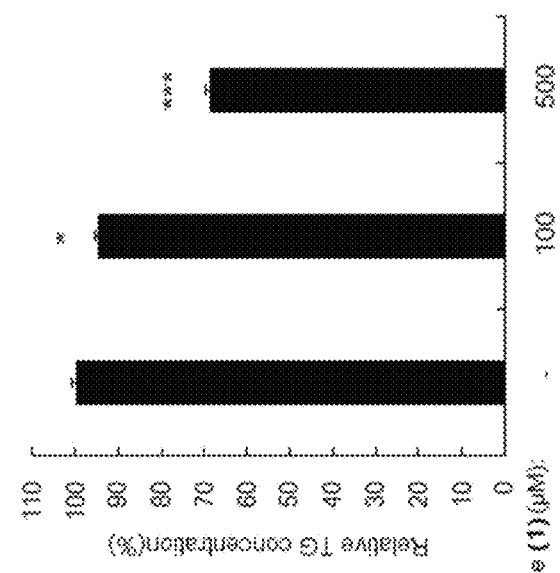
FIG. 2 shows an inhibitory effect of (+)-isonitramine (1) according to another embodiment on a fat content.
Figure 2:
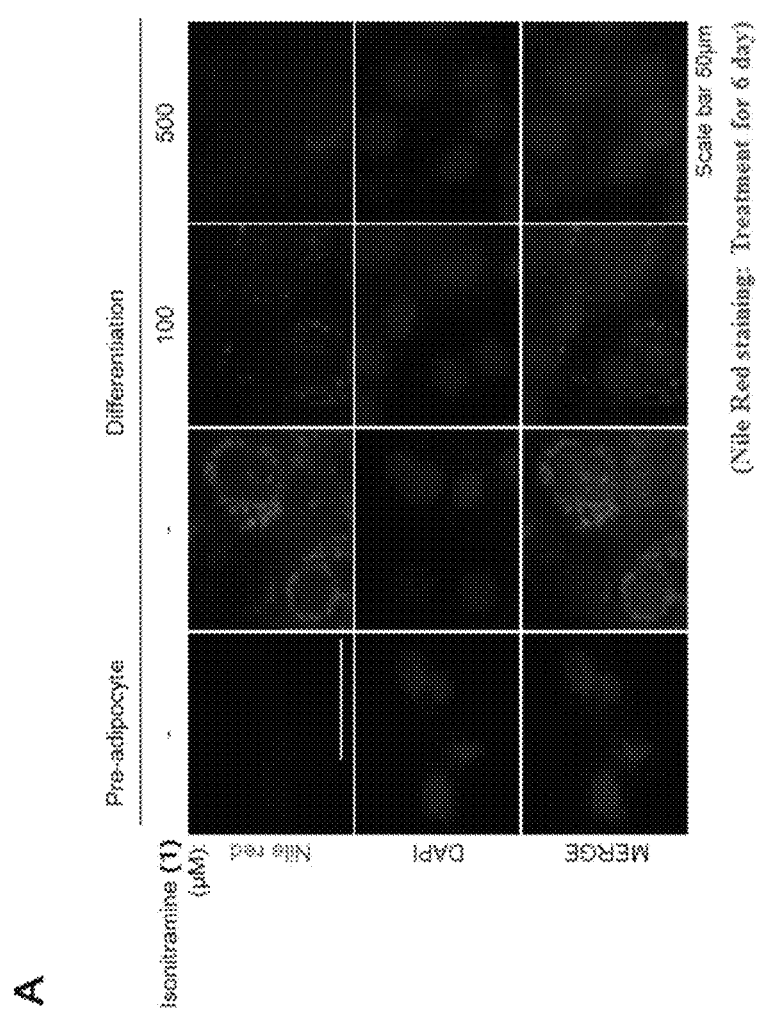

As a result of confirming the inhibitory effects of (+)-isonitramine (1), which was synthesized according to Example 1, on fat accumulation and adipocyte differentiation, it was confirmed that (+)-isonitramine (1) inhibited the differentiation of the 3T3-L1 mouse preadipocytes into mature adipocytes as shown in FIG. 2A, and that (+)-isonitramine (1) decreased the concentration of triglyceride in a concentration-dependent manner as shown in FIG. 2B.

Figure 3:
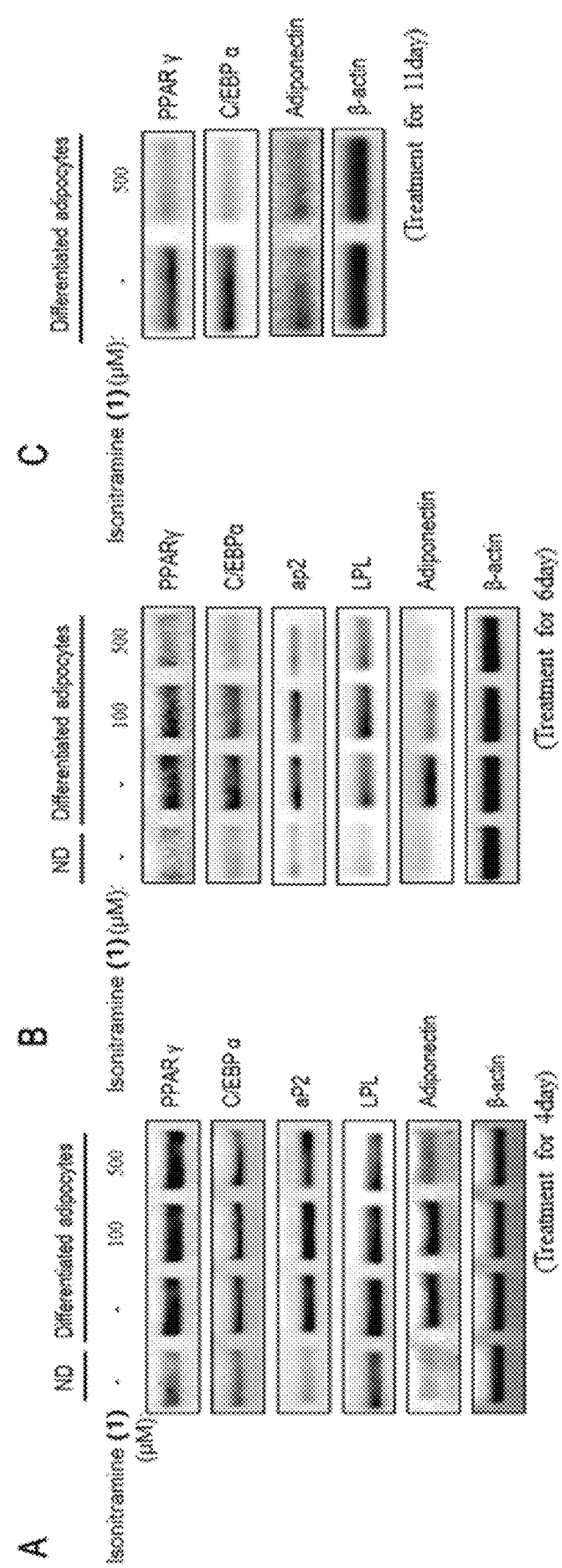
FIG. 3 shows an inhibitory mechanism of (+)-isonitramine (1) of FIG. 2 on differentiation of an adipocyte.

Furthermore, as shown in FIG. 3, the mRNA expression of each of PPARγ that are responsible for the differentiation of adipocytes and C/EBPα that promotes biosynthesis of fat and differentiation of adipocytes was inhibited without cytotoxicity, wherein PPARγ is known to induce adverse effects, such as obesity and fatty liver, when over-expressed. In addition, the mRNA expression of aP2, LPL, and adiponectin, which is regulated by PPARγ and C/EBPα as transcript factor, was weakened.

Therefore, it was confirmed that the isonitramine stereoisomer of the present disclosure had effects on the prevention or treatment of obesity related to fat accumulation.

<Example 3> Antidiabetic Effects of Isonitramine Derivatives

A glucose assay kit was purchased for use from Youngdong Company (Seoul, Korea). In addition, from Sigma Company, porcine α-amylase, yeast α-glucosidase, 3,5-dinitrosalicylic acid (DNS), p-nitrophenol glucoside (pNPG), rat intestinal acetone powder, sucrose, and maltose were purchased. Soluble starch was obtained from Samchun Chemical Company (Seoul, Korea), and Acarbose was purchased from Tokyo chemical industry Company (Tokyo, Japan).

1. Analysis of Inhibitory Effect of Porine α-Amylase

5 μl of α-amylase (0.1 U/mL) was diluted with 50 mM phosphate buffer (pH 6.8), and the diluted solution was mixed with each of 100 μM (+)-isonitramine (1) or Compound 2 to 6 of Example 1. In addition, as a positive control group, Acarbose was mixed at the same concentration with (+)-isonitramine (1).

The mixtures were pre-cultured at a temperature of 37° C. for 10 minutes, and 25 μl of 0.5% starch solution was added thereto, followed by being cultured at a temperature of 37° C. for 10 minutes. Then, the mixtures were cultured again at a temperature of 100° C. for 5 minutes to stop the reaction, and the mixtures were cooled.

25 μl of DNS was added to the cooled reaction solutions, and a color reaction was induced at a temperature of 100° C. for 5 minutes. The resulting solutions were cooled again. The solutions in which the color reaction was induced were transferred to a 96-well plate, and absorbance thereof was measured at a wavelength of 540 nm by using a 96-well microplate reader.

Here, the inhibitory effect was calculated according to Equation 1:

$$\text{Enzymatic inhibitory activity} = (1 - A_x/A_0) \times 100\% \quad [\text{Equation 1}]$$

$A_x$ indicates an absorbance value of a control group $A_0$ indicates an absorbance value of a test group upon treatment of isonitramine 2. Analysis of Inhibitory Effect of Yeast α-Amylase 5 μl of α-amylase (0.1 U/mL) was diluted with 50 mM sodium acetate buffer (pH 5.6), and the diluted solution was mixed with each of 100 μM (+)-isonitramine (1) or Compound 2 to 6 of Example 1. In addition, as a positive control group, Acarbose was mixed at the same concentration with (+)-isonitramine (1).

The mixtures were pre-cultured at a temperature of 37° C. for 10 minutes, and 25 μl of pNPG was added thereto, followed by being cultured at a temperature of 60° C. for 10 minutes. Then, 1N NaOH was added thereto to stop the reaction.

Afterwards, the resulting solution in which a color reaction was induced was transferred to a 96-well plate, and absorbance thereof was measured at a wavelength of 405 nm by using a 96-well microplate reader.

3. Analysis of Inhibitory Effect of Rat Intestinal Acetone Powder

First, 100 mg of rat intestinal acetone powder was added to 3 ml of 0.9% NaCl solution, and a homogenizing process was performed thereon for 5 minutes in the ice. The mixed solution was subjected to centrifugation at a speed of 12,000 rpm for 30 minutes, and then, the supernatant was removed therefrom and the precipitate was transferred to a 15 ml tube.

Then, 50 μl of enzyme solution was mixed with (+)-isonitramine (1), and as a positive control group, Acarbose was mixed at the same concentration with (+)-isonitramine (1). Each of the mixtures was cultured at a temperature of 37° C. for 5 minutes.

Meanwhile, for use as a substrate, 1 mM pNPG, 56 mM sucrose, and 5 mM maltose were dissolved in 0.1M PBS (pH 7.0). 50 μl of the substrate was added to the cultured mixtures, and cultured at a temperature of 37° C. for 5 minutes.

5 μl of the reaction solution was then mixed with 500 μl of glucose trinder kit solution, and cultured at a temperature of 37° C. for 5 minutes. The resulting solution in which a color reaction was induced was cultured at a temperature of 100° C. for 2 minutes to stop the reaction, and then, transferred to a 96-well plate. Then, absorbance thereof was measured at a wavelength of 570 nm.

To measure the glucose standard curve, D-glucose was diluted with 0.1M PBS (pH 7.0) to various concentrations (0 to 480 mg/dL).

5 μl of glucose reference solution was mixed with 500 μl of glucose trinder kit solution, and cultured at a temperature of 37° C. for 5 minutes. The resulting solution in which a color reaction was induced was cultured at a temperature of 100° C. for 2 minutes to stop the reaction, and then, transferred to a 96-well plate. Then, absorbance thereof was measured at a wavelength of 570 nm.

4. Measurement of Zebrafish Pancreatic Toxicity 5-day-old zebrafish larvae (ins:EGFP larvae) were added to a 96-well plate, and reacted with (+)-isonitramine (1) of Example 1 at a temperature of 27° C. for 24 hours. Then, each larva was put to a fresh E3 solution, in which 500 μM alloxan (available from Sigma, St. Louis, Mo., USA) was added or not added, for 30 minutes.

After 30 minutes, all larvae were fixed with 4% paraformaldehyde (PFA) at room temperature for 50 minutes. A washing process using PBS was performed thereon, and fluorescence images of insulin showing expression of pancreatic islets were obtained by using a phase contrast microscope (Axiovert M200 microscope, Zeiss).

Afterwards, the pixel intensity of the pancreas was measured by using Image J software, as a percentage of the region of enhanced green fluorescent protein (EGFP), and statistically compared and recorded.

5. Management of Postprandial Hyperglycemia in Diabetic-Inducible Zebrafish

The zebrafish was anesthetized by placing it in water at a temperature of 8° C. for 20 seconds.

For intraperitoneal injection, 350 mg/kg of a solution of 0.9% streptozocin (available from Sigma, St. Louis, Mo.) in 0.09% NaCl solution was injected with a syringe having 25 gauge needle (available from Trajan Scientific, Australia). Here, to a control group of zebrafish, the same amount of PBS was injected intraperitoneally. After the completion of the injection, the test and control groups of zebrafish were bread at a temperature of 24° C.

The zerafish was subjected to intraperitoneal injection of STZ or PBS three times (350 mg/kg) for a week. After the final injection, the zerafish was fed with commercial flake food (available from Tetrabits tropical flakes, Tetra, Germany) for 5 days.

After fasting for 24 hours, the zebrafish to which PBS was injected was fed with commercial flask food, and the zebrafish to which STZ was injected was fed with flake mixed with (+)-isonitramine (1) at various concentrations, for 1 hour. Afterwards, plasma blood of each zebrafish was enzymatically measured by using a glucose trinder kit.

6. Experiment Results

Figure 4:
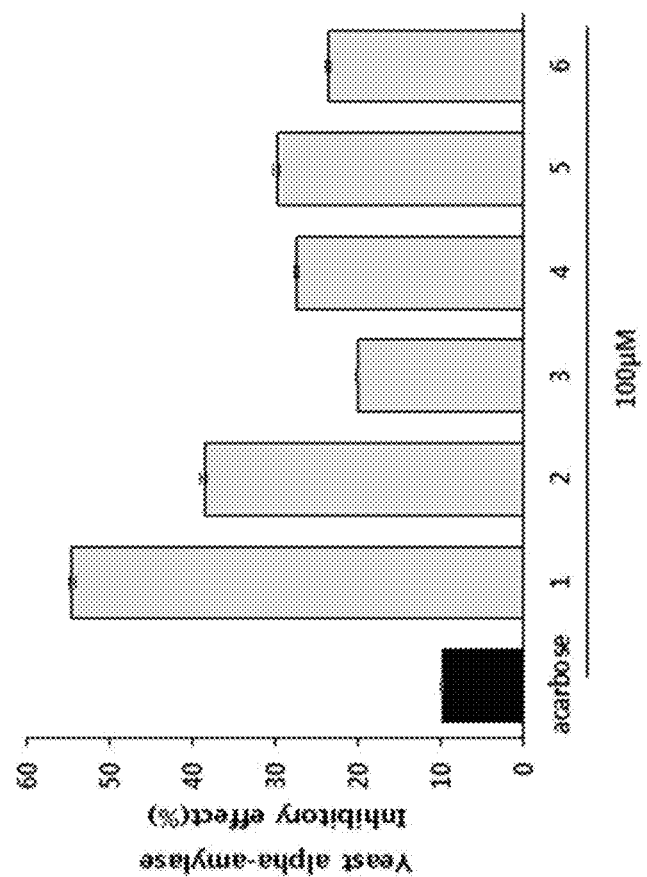
FIG. 4 is a bar graph showing an inhibitory effect of (+)-isonitramine (1) according to another embodiment or Compounds 2 to 6 on activity of a carbohydrate metabolism enzyme.
Figure 4:
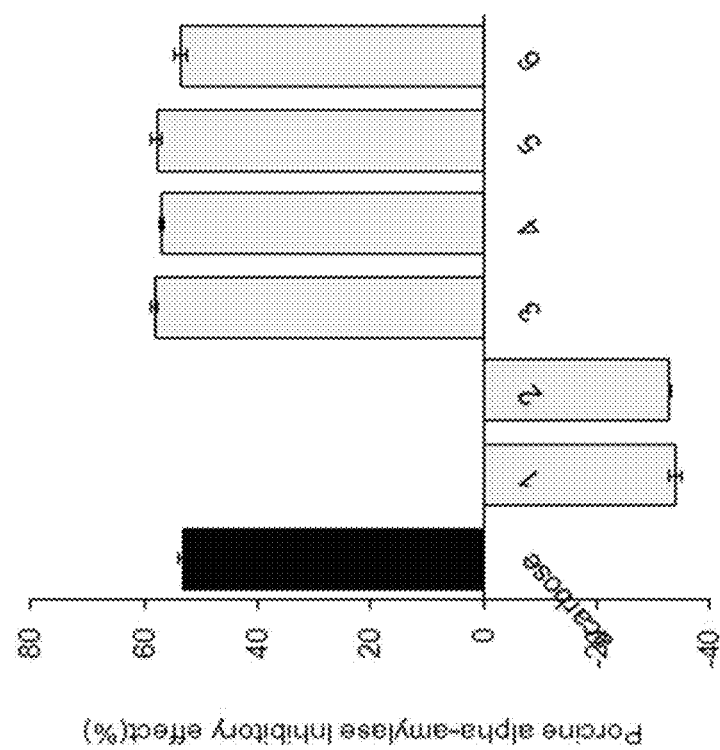

As a result of confirming antidiabetic effects of (+)-isonitramine (1) and Compound 2 to 6 synthesized according to Example 1 and as shown in FIG. 4, it was confirmed that (+)-isonitramine (1) and Compound 2 had selective inhibitory effects on metabolic enzymes essential for carbohydrate absorption, as compared with Compound 4 to 6. In particular, it was also confirmed that (+)-isonitramine (1) hardly inhibited α-amylase while inhibiting α-glucosidase, and there was little concern about side effects, such as abdominal distension and diarrhea of the existing drug, Acarbose.

Figure 5:
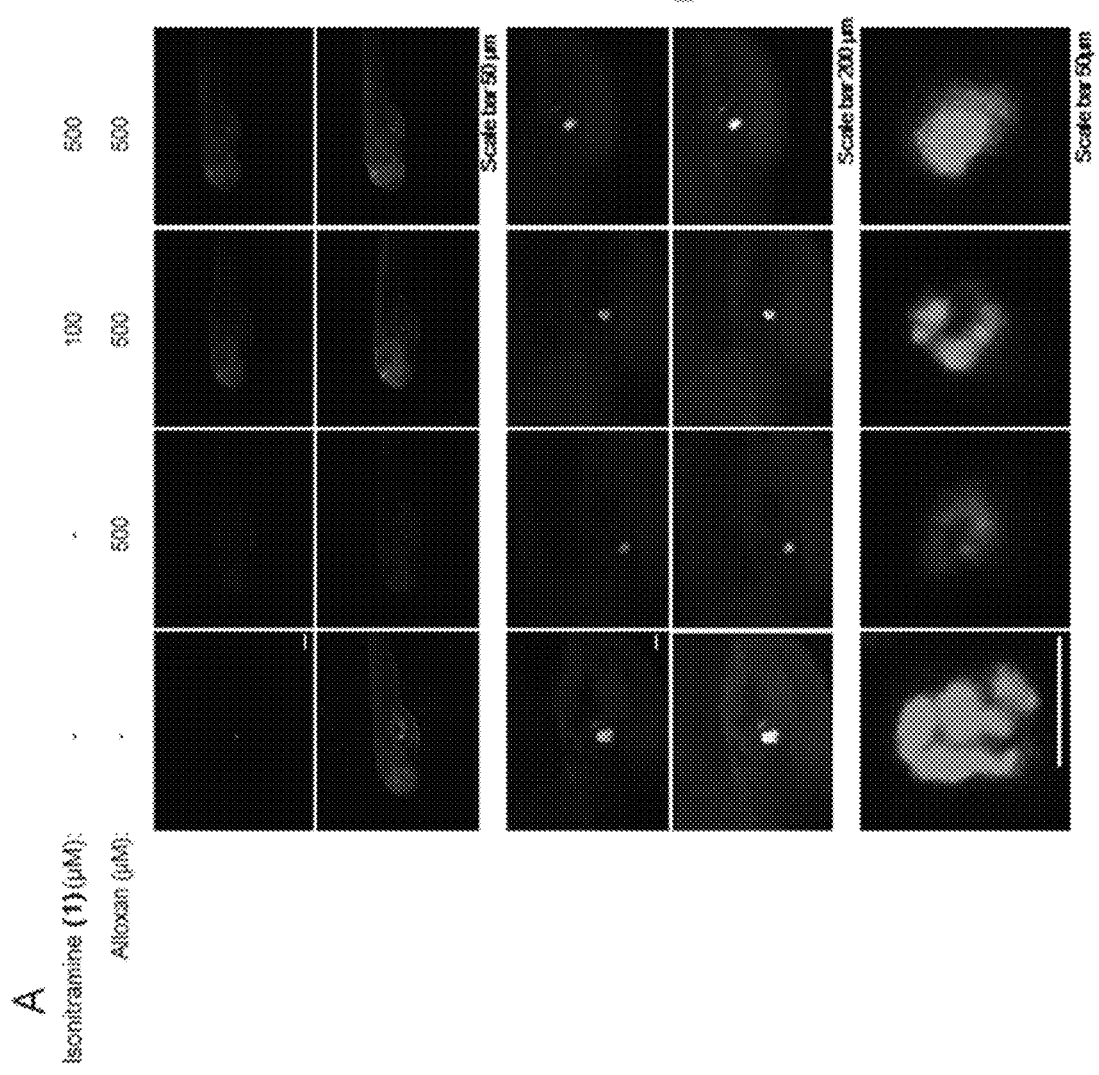
FIG. 5 shows an effect of (+)-isonitramine (1) of FIG. 4 on protection of pancreas.
Figure 5:
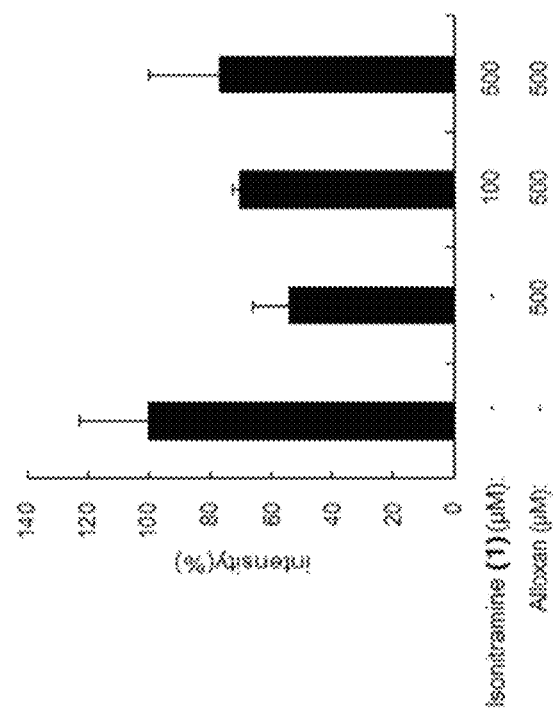
Figure 6:
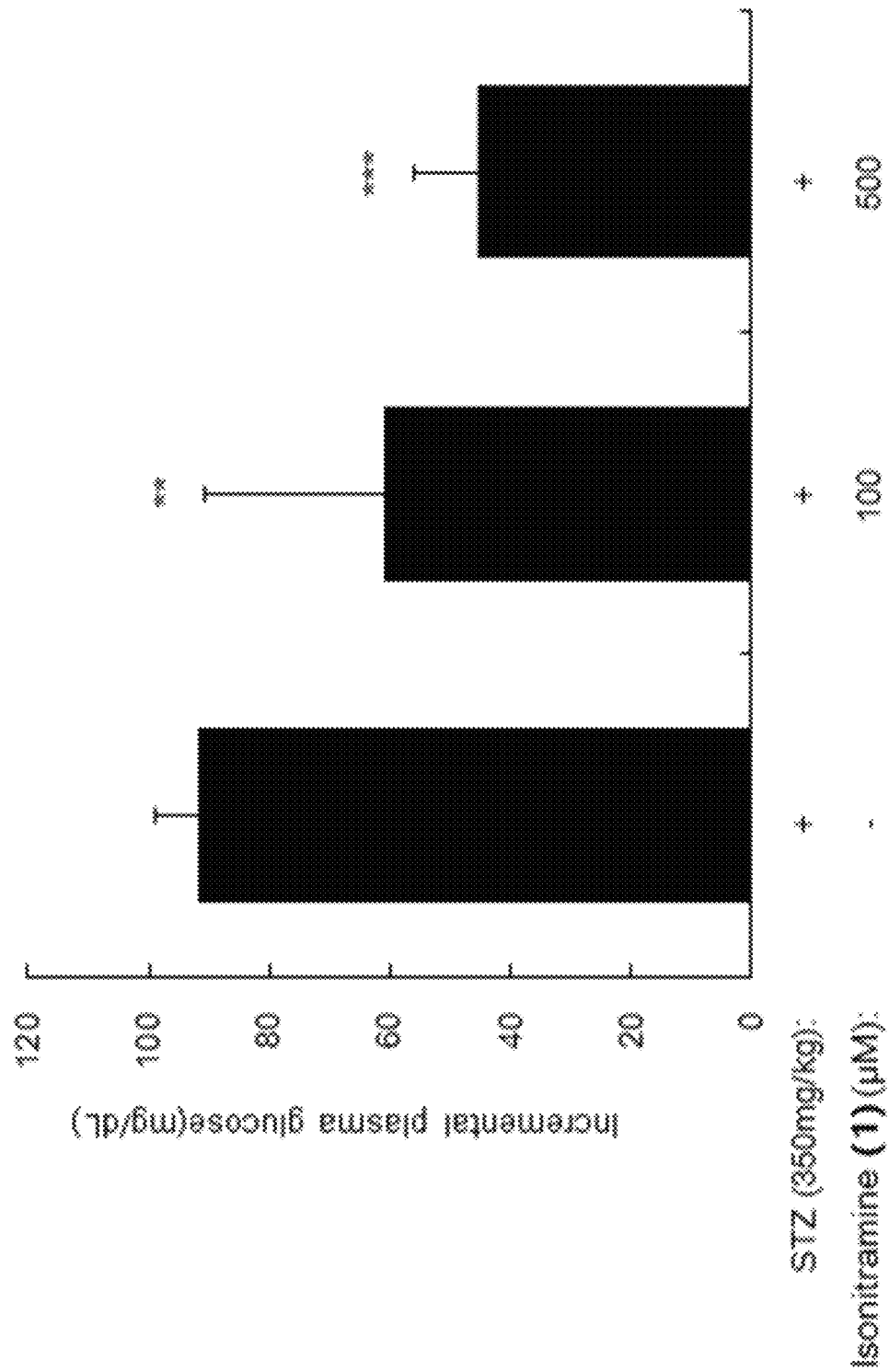
FIG. 6 is a bar graph showing an inhibitory effect of (+)-isonitramine (1) of FIG. 4 on blood sugar.

Furthermore, as shown in FIG. 5, it was confirmed that (+)-isonitramine (1) had no developmental toxicity and cardiovascular toxicity in the model of zerafish. As shown in FIG. 6, it was also confirmed that (+)-isonitramine (1) exhibited effects on the reduction of blood glucose in a concentration-dependent manner.

<Example 4> Effects of Isonitramine Derivatives on Insulin Secretion

1. Cell Culture

To identify effects of isonitramine derivatives on insulin secretion, a type of insulin cells, e.g., HIT-T15 cells, were obtained by the Korean Cell Line Back, and then, subcultured. In detail, the HIT-T15 cells were cultured in a RPMI1640 medium (available from invitrogen. Co, USA) supplemented with 10% fetal bovine serum (FBS, available from invitrogen. Co, New Zealand 10091-148), 100 mu/ml of penicillin, and 100 μg/ml of streptomycin, under humidification conditions of a temperature of 37° C. and 5% $CO_2$.

2. Measurement of Insulin Secretion

Insulin secretion influenced by (+)-isonitramine was measured according to the recommended method using insulin ELISA kit (Cat.10-1113-01, available from Mercodia Company). First, the HIT-T15 cells were loaded to a 96-well plate at a concentration of $5 \times 10^4$ cells/well, and cultured until reaching 70% to 80% cell confluency in an incubator at a temperature of 37° C. in a $CO_2$ incubator. Then, the cells were pre-treated with 500 μM alloxan, which induces a pancreatic-specific toxic response, for 30 minutes. Afterwards, (+)-isonitramine was added to each well, and cultured for 24 hours. The culture solution was collected therefrom, and subjected to a centrifugation at a speed of about 15,000 rpm for 3 minutes. The cells were precipitated and the supernatant was accordingly prepared therefrom. 25 μl of the supernatant was added to each well of the ELISA kit, and 100 μl of enzyme conjugate solution was also added thereto and allowed to rest for 1 hour on a plate shaker, so as to induce an antigen-antibody reaction. After an hour, the supernatant was removed therefrom, and a washing buffer (350 μl) was used to wash non-specifically bound proteins or unbound proteins. Here, 200 μl of a substrate (TMB) was added and allowed for an enzymatic reaction at room temperature for 15 minutes. Then, 50 μl of a stop solution was added thereto to terminate the reaction. The changes resulted from the termination of the reaction were measured by using an ELISA-reader (VERSA max, micro-reader, MDS. Co, USA) at a wavelength of 450 nm.

3. Experiment Results

Figure 7:
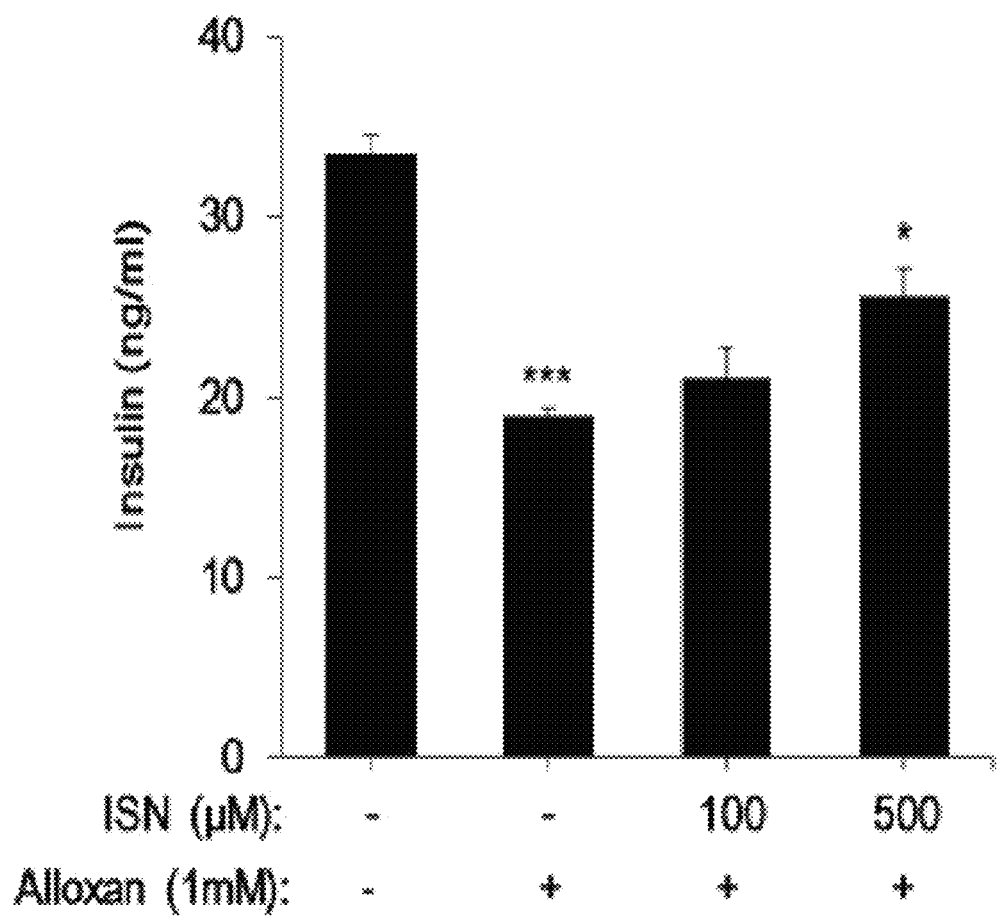
FIG. 7 is a bar graph shows a promoting effect of (+)-isonitramine (1) according to an embodiment on secretion of insulin.

The results showing the effects of (+)-isonitramine synthesized according to Example 1 on the insulin secretion are shown in FIG. 7.

Referring to FIG. 7, insulin secreted in a normal state was measured as 33.39±1.12 ng/mL (n=4), but it was confirmed that, when treated with alloxan, the insulin secretion was reduced to 18.92±0.43 ng/mL. That is, isonitramine showed an effect of increasing the insulin secretion in a concentration-dependent manner.

<Example 5> Effects of Isonitramine Derivatives on Regulation of Metabolic Hormones 1. Cell Culture A zebrafish embryo is a model system that has been recently widely used in the fields of metabolic studies. In particular, due to a metabolism in a manner very similar to that of the human body in terms of glucose regulation, the zebrafish embryo is widely used in the fields of diabetes and glucose metabolism research. Regarding the glucose metabolism, a zerafish embryo was used to verify an effect of isonitramine on the expression of phosphoenolpyruvate carboxykinase (PEPCK), which is a key enzyme for regulating the first stage of gluconeogenesis, and insulin.

In the experiment performed to verify the effect on the amount of insulin secretion, the zebrafish embryo underwent 96 hour post-fertilization (hpf) was exuviated, and then, treated with isonitramine for 48 hours. In the experiment performed to verify the effect on gluconeogenesis, 100 mM cyclic AMP (cAMP) and 100 mM dexamethasone (DEX) were simultaneously treated with isonitramine, and then, cultured for 48 hours.

2. Measurement of Insulin Secretion and Expression of PEPCK

From the cultured embryo above, TRIzol (available from Invitrogen) was used to isolate mRNA, and the isolated RNA was synthesized to cDNA by using iScript cDNA Synthesis Kit (available from Bio-Rad). Afterwards, to amplify the cDNA, primers listed in Table 2 were used, wherein each primer was purchased from Bioneer.

TABLE 2

| Name | Direction | Sequence | SEQ ID NO: |
|---|---|---|---|
| zf PEPCK | Forward | GAGAATTCTCACACACAC ACACGTGAGCAGTA | 13 |
|  | Reverse | GTAAAAGCTTTCCGCCATAACATC TCCAGCAGAA | 14 |
| zf prepro-insulin (insa) | Forward | AGTGTAAGCACTAACCCAGGCACA | 15 |
|  | Reverse | TGCAAAGTCAGCCACCTCAGTTTC | 16 |
| zf β-actin | Forward | CGAGCAGGAGATGGGAACC | 17 |
|  | Reverse | CAACGGAAACGCTCATTGC | 18 |

In the PCR amplification, β-actin was used as an internal control group. The PCR products were separated by using 2.0% agarose gel, followed by being visualized by RedSafe nucleic acid staining (available from Intron, Korea) and UV irradiation.

3. Experiment Results

Figure 8:
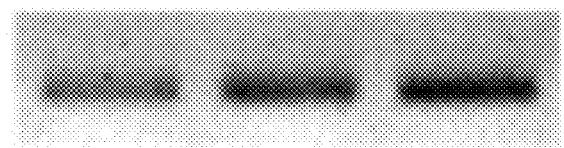
FIG. 8 shows a promoting effect of (+)-isonitramine (1) according to another embodiment on secretion of insulin.
Figure 8:
Figure 9:
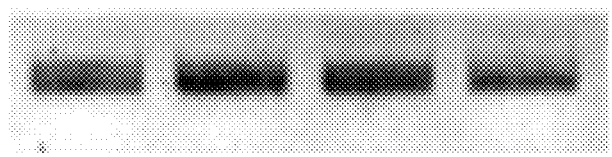
FIG. 9 shows an inhibitory effect of (+)-isonitramine (1) of FIG. 8 on PEPCK.
Figure 9:
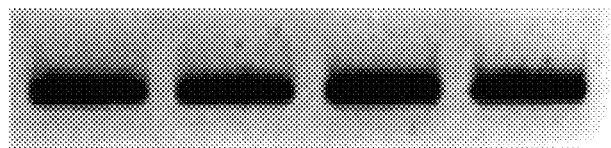

The results showing the effects of (+)-isonitramine synthesized according to Example 1 on the insulin secretion and the expression of PEPCK are shown in FIGS. 8 and 9.

Referring to FIG. 8, as the concentration of isonitramine increased, the expression of insulin also increased. Referring to FIG. 9, the inhibitory effect of isonitramine on the expression of PEPCK was significantly increased in proportion to the concentration of isonitramine.

That is, taking the results of Examples 4 and Example 5 together, it was confirmed that isonitramine and a pharmaceutical composition and a health food, which include isonitramine, promoted the expression insulin and inhibited gluconeogenesis at the same time, thereby exhibiting effects of reducing blood glucose.

Hereinafter, Preparation Examples of a composition including the isonitramine stereoisomer of the present disclosure or a racemic mixture of the isonitramine stereoisomers will be described. However, the present disclosure is not intended to be limited thereto, but is specifically described as below.

<Preparation Example 1> Preparation of Pharmaceutical Composition

<Preparation Example 1-1> Preparation of Powders 20 mg of (+)-isonitramine, 100 mg of lactose, and 10 mg of talc were mixed together, and powders thereof were prepared by packing the mixture in an airtight bag.

<Preparation Example 1-2> Preparation of Tablets 1 mg of (+)-isonitramine, 100 mg of corn starch, 100 mg of lactose, and 2 mg of magnesium stearate were mixed together, and tablets thereof were prepared by a tabletting process according to a conventional method.

<Preparation Example 1-3> Preparation of Capsules 10 mg of (+)-isonitramine, 100 mg of corn starch, 100 mg of lactose, and 2 mg of magnesium stearate were mixed together, and capsules thereof were prepared by a capsulating process according to a conventional method.

<Preparation Example 1-4> Preparation of Injections 10 mg of (+)-isonitramine, a suitable amount of sterilized and distilled water for injection, and a suitable amount of pH adjuster were mixed together, and injections containing the above-described ingredient contents per ampoule (2 ml) according to a conventional method of preparing injections.

<Preparation Example 1-5> Preparation of Ointment 10 mg of (+)-isonitramine, 250 mg of PEG-4000, 650 mg of PEG-400, 10 mg of white vaseline, 1.44 mg of methyl para-hydroxybenzoate, 0.18 mg of propyl para-hydroxybenzoate, and the remaining amount of purified water were mixed together, and an ointment thereof was prepared according to a conventional method of preparing an ointment.

<Preparation Example 2> Health Supplement Food

<Preparation Example 2-1> Preparation of Health Food 1 mg of (+)-isonitramine, a suitable amount of vitamin mixtures (70 μg of Vitamin A acetate, 1.0 mg of Vitamin E, 0.13 mg of Vitamin B1, 0.15 mg of Vitamin B2, 0.5 mg of Vitamin B6, 0.2 μg of Vitamin B12, 10 mg of Vitamin C, 10 μg of Biotin, 1.7 mg of nicotinamide, 50 μg of folic acid, and 0.5 mg of calcium pantothenate), and a suitable amount of inorganic mixtures (1.75 mg of ferrous sulfate, 0.82 mg of zinc oxide, 25.3 mg of magnesium carbonate, 15 mg of monobasic potassium phosphate, 55 mg of dibasic calcium phosphate, 90 mg of potassium citrate, 100 mg of calcium carbonate, and 24.8 mg of magnesium chloride) were mixed together, and granules thereof were prepared. Then, a health food containing the same was prepared according to a conventional method.

<Preparation Example 2-2> Preparation of Health Drink 1 mg of (+)-isonitramine, 1,000 mg of citric acid, 100 g of oligosaccharide, 2 g of pulm concentrate, 1 g of taurine, and purified water were prepared to make a total of 900 ml, and the above ingredients were mixed according to a conventional method of preparing health drink. The mixture was stirred and heated at a temperature of 85° C. for about 1 hour, and then, the resulting solution was filtered. The filtrate was put in a sterilized 2 L container, and the container was then sealed and sterilized, and refrigerated.

While the present disclosure has been particularly shown and described with reference to specific embodiments thereof, one of ordinary skill in the art will readily appreciate that the embodiments provided herein may be embodied in many different forms and should not be construed as being limited to the embodiments set forth herein. Therefore, the substantial scope of the present disclosure will be defined by the appended claims and equivalents thereof.

What is claimed is:

1. A method of treating a metabolic disease in a subject in need thereof, comprising:

providing a pharmaceutical composition comprising, as an active ingredient, a stereoisomer represented by Formula 1 or a racemic mixture thereof:

[Formula 1]

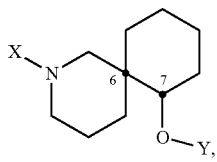

wherein, in Formula 1,
X is a hydrogen atom;
Y is a hydrogen atom;
carbon atoms at the $6^{th}$ position and the $7^{th}$ position are each a chiral center; and
administering the pharmaceutical composition to the subject, wherein the metabolic disease is treated,
wherein the metabolic disease is selected from the group consisting of obesity, diabetes, hyperglycemia, insulin resistance, and hyperinsulinemia.

2. A method of treating a metabolic disease in a subject in need thereof, comprising:

providing a health food comprising, as an active ingredient, a stereoisomer represented by Formula 1 or a racemic mixture thereof:

[Formula 1]

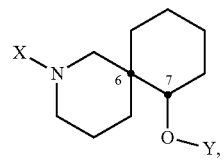

wherein, in Formula 1,
X is a hydrogen atom;
Y is a hydrogen atom;
carbon atoms at the $6^{th}$ position and the $7^{th}$ position are each a chiral center; and
administering the health food to the subject, wherein the metabolic disease is treated,
wherein the metabolic disease is selected from the group consisting of obesity, diabetes, hyperglycemia, insulin resistance, and hyperinsulinemi.

* * * * *